United States Patent [19]

Minten

[11] Patent Number: 5,716,378
[45] Date of Patent: Feb. 10, 1998

[54] HEART PRESERVATION AND TRANSPORTATION APPARATUS AND METHOD EMPLOYING LOW RATE CARDIAC PACING FOR IMPROVED REMOVAL OF CATABOLITES FROM THE MYOCARDIUM

[75] Inventor: Jaak M. O. Minten, Landen, Belgium

[73] Assignee: Medtronic, Inc., Minneapolis, Minn.

[21] Appl. No.: 660,786

[22] Filed: Jun. 6, 1996

[51] Int. Cl.$^6$ .............................. A61N 1/362; A01N 1/02
[52] U.S. Cl. .................................................. 607/3; 435/283
[58] Field of Search ............................ 607/1, 2, 3; 435/1, 435/283, 284

[56] References Cited

U.S. PATENT DOCUMENTS

| | | |
|---|---|---|
| 5,051,352 | 9/1991 | Martindale et al. |
| 5,338,662 | 8/1994 | Sadri. |
| 5,356,771 | 10/1994 | O'Dell. |
| 5,391,142 | 2/1995 | Sites et al. |

OTHER PUBLICATIONS

"Pathophysiologic of features of biological preservation of the heart using the Robirek technic" [translation], Journal article—Patol Fiziol Eksp Ter (USSR) Sep.–Oct. 1979, (5) pp. 15–20, ISSN 0031–2991, Barinof EF [author].

"Evaluation of the functional state of the heart transplant 20–24 hours after biological preservation" [translation], Journal article—Fiziol Zh (USSR) Mar.–Apr. 1988, 34 (2) pp. 51–56, ISSN –0201–8489, EWR, Barinov EF [author].

"Isolated working rat heart perfusion with perfluorochemical emulsion Fluosol–43", Segal et al [authors], The American Physiological Society, 1982.

"Prolonged support of working rabit hearts using Fluosol–43 or erythrocyte media", Segal et al [authors], The American Physiological Society, 1987.

"Fluorochemical emulsion APE–LM substantially improves cardiac preservation", Segel et al [authors], American Physiological Society, 1992.

"Long term heart preservation by intermittent perfusion with crystalloid medium", Segal et al [authors], Cardiovasc. Surg., 1993:106:811–22.

"Importance of Substrate Enhancement for Long–term Heart Preservation", Segal et al [authors], J.Heart Lung Transplant, 1993:12:613–23.

"Posttransplantation Function of Hearts Preserved with Fluorochemical Emulsion", Segal et al [authors], J.Heart Lung Transplant 1994:13:669–80.

*Primary Examiner*—Scott M. Getzow
*Attorney, Agent, or Firm*—Michael J. Jaro; Harold Patton

[57] ABSTRACT

A system and method for preservation and transport of a donor heart are provided, which includes features for improving the refreshment of the myocardium and for removing toxic catabolites, thereby lengthening the available time for effective transport. The invention utilizes a housing with a perfusion subsystem for retrogradely perfusing the heart, and a subsystem for maintaining the heart in a moderate hypothermic state, preferably at about 10–25 C. A pacemaker is utilized to pace the heart at a below normal rate, preferably in the range of 2–40 bpm, and more preferably 15–30 bpm, so as to continuously squeeze out catabolites and refresh the myocardium with the perfusion fluid. The system can be portable, where the heart can be maintained with or without dialysis; when the apparatus is not being transported, it utilizes power line energy and is adapted to provide dialysis.

30 Claims, 3 Drawing Sheets

HEART PRESERVATION AND TRANSPORTATION APPARATUS AND METHOD EMPLOYING LOW RATE CARDIAC PACING FOR IMPROVED REMOVAL OF CATABOLITES FROM THE MYOCARDIUM

BACKGROUND OF THE INVENTION

1. Field of the Invention

This invention relates to organ preservation devices and, in particular, preservation devices for donor hearts which have the capability of maintaining the heart in a hypothermic state, perfusing it, and pacing it so as to optimally remove catabolites.

2. Description of the Prior Art

Heart preservation has been a subject of investigation for at least several decades, since the development of the technique of heart transplant from a donor to a patient with a failing heart. The aim is to be able to preserve the cardioplegic heart for as long as possible, and do it such that the heart is fully functional upon being transplanted to the recipient. Typically, the excised donor heart is preserved following cardioplegic arrest in a fluid filled bag, with or without intermittent or continuous perfusion, and chilled on ice or otherwise maintained at a reduced temperature to keep it in a lower state of metabolism. Preservation time is nominally limited to about 4 hours, which restricts donor delivery to within the continent or even within the country or state of the donor. Functional recovery upon normothermic reperfusion depends upon the circumstances of preparation of the heart and the preservation, e.g., whether there was quick and uniform myocardial cooling; the cardioplegic solution used; myocardial resistance; uniform interstitial (re)perfusion; absence or quick passage of the arrhythmogenic phase; etc.

Different designs of heart preservation apparatus have been demonstrated. U.S. Pat. No. 5,338,662, titled Organ Perfusion Device, illustrates apparatus for perfusing organs such as a heart, by controlling perfusion fluid pressure and flow parameters. Other references discuss factors such as temperature at which the heart is preserved and the perfusion fluid used. Portable devices have been developed allowing the perfusion preservation of the donor heart while controlling perfusion pressure, oxygenation, temperature, pH, and other parameters. Experimental studies have been reported where hearts of rabbits and rats have been paced at rates in the range of 180–325 bpm while being preserved. Normothermic preservation, i.e., using an ex vivo beating (working or Langendorff perfused) heart, has been experimentally explored but never practically applied.

Experimental results which have been reported show that acceptable preservation can be prolonged by a number of factors. A first important factor is the cardioplegic solution used, i.e., an intracellular or extracellular type of solution, with or without additives for purposes such as quick contractility arrest and reducing coronary resistance. A second factor is the rate of cooling during cardioplegic arrest, where uniform myocardial cooling (and perfusion) is more important than the quickness of cooling and induction of cardiac arrest. A third factor is the level of myocardial cooling during preservation, i.e., normothermia (ex-vivo beating heart, at 25–37 C.); moderate hypothermia (10–25 C.); or deep hypothermia (0–10 C.). Normothermia results in maintenance of a high catabolism of energy rich phosphates, such that it is difficult to maintain an equilibrium between energy supply and consumption; deep hypothermia can have deleterious effects on the integrity of the cellular membrane and thus on myocardial cell survival. A fourth factor is the preservation method itself, e.g., hypothermic submersion storage (typically on ice), with antegrade or retrograde, low or high pressure, intermittent or continuous coronary perfusion preservation. Continuous low pressure retrograde coronary perfusion has been found in multiple studies to be the preferable method.

Another factor pertinent to effective preservation is the type of preservation fluid, or solution present interstitially during storage or perfusion. The solution has a bearing on, e.g., the intra- and extracellular concentrations of ions, the energy supply (energy rich molecules and oxygen), the integrity of cellular membranes and ion-pumps, myocardial resistance, etc. Coronary dilation has been shown to improve cardiac preservation, presumably because of improved perfusion of all or more of the interstitial spaces. Maintenance of adequate coronary perfusion has been associated with the degree of functional recovery upon normothermic reperfusion, whereas a gradual increase of the myocardial resistance, as a result of oedema formation or coronary spasm, reduces the chances of adequate cardiac functioning after preservation. Likewise, the level or arrhythmogenity and the likelihood of defibrillating the heart successfully upon normothermic reperfusion is a strong determinant of the final outcome and success of the transplantation.

Optimization of the above factors helps with maintenance of low levels of metabolic breakdown products, e.g., lactate, which, if not adequately perfused, accumulate in inter- and intracellular (micro) spaces and can reach locally toxic levels, thus highly influencing the functional recovery upon normothermic reperfusion of myocardial cells in a micro or macro region depending on the distribution of the intolerable levels. However, maintenance of perfusion and thus adequate removal of catabolites has remained a substantial and limiting problem in this area. Development of heart preservation apparatus has focussed on simplifying and improving the perfusion function, such as by use of improved compositions of perfluorochemical solutions, limiting the volume of the perfusion fluid, and continuously controlling the fluid in a closed loop system. However, even with these improvements, a wash out of accumulated catabolites can be measured upon normothermic reperfusion, indicating inadequate interstitial perfusion and refreshment of preservation solution in all myocardial areas. What has been lacking, and what this invention provides, is an enhanced mechanism for removal of interstitially accumulated catabolites, i.e., products of metabolism.

SUMMARY OF THE INVENTION

It is an object of this invention to enhance removal of catabolites from a perfused donor heart, so as to prolong the preservation function and yield a better functioning heart upon transplantation to a recipient. The approach of this invention recognizes that in order to assure adequate fluid refreshment in all parts of the myocardial wall, the interstitial space needs to be squeezed by the cardiac muscle itself, i.e., the heart needs to beat so that the contractions can squeeze out accumulated catabolites and assure appropriate refreshment of perfusion fluid in all interstitial spaces. But normothermic preservation of an ex vivo beating heart means that the metabolism remains high, with the consequent problem of too high a production of catabolites. In order to reduce metabolism, the heart must be cooled to a hypothermic state, where the heart can be paced so as to maintain cardiac beating. However, in deep hypothermia, i.e., less than 10 C., the heart can not be paced. These considerations lead to the conclusion of using moderate hypothermia, e.g., 10-25 C., where the excised heart can be effectively paced. At this moderate range of hypothermic temperatures, pacing is best carried out at low rates, below normal pacing rates, preferably 2-40 bpm, and more preferably 15-20 bpm.

In accordance with the above, the invention provides apparatus, preferably portable at least in part, and a method for preserving and transporting a donor heart, which may be a cardioplegic heart. The heart is preserved in a vessel which contains a perfusion fluid, preferably a perfluorochemical solution. A perfusion fluid circulating system circulates the perfusion fluid in a retrograde direction through the coronary arteries of the submerged heart, the fluid being delivered under constant moderate pressure to the aorta just outside of the aortic valve, so that fluid is perfused into the coronary ostia and through the coronary arteries. The circulating system contains a pump subsystem, preferably battery-powered, for pumping the fluid, and also contains continuously operable control elements for maintaining the fluid at a temperature in the moderate hypothermic range, as well as providing dialysis, pH control, oxygenation control, and for performing other functions as needed for complete preservation of the heart, such as micro-pore fluid filtering. A cardiac pacing subsystem is employed for pacing the heart, preferably in a dual or quadruple chamber asynchronous mode, at a rate less than the normal range and preferably within the range of 2-40 bpm, to facilitate removal of catabolites. The system and method preferably also include use of a standby defibrillator subsystem for defibrillating the heart if it goes into atrial or ventricular fibrillation; the system also can include means to detect and treat atrial and ventricular tachycardia.

DESCRIPTION OF THE PREFERRED EMBODIMENTS

Figure 1:
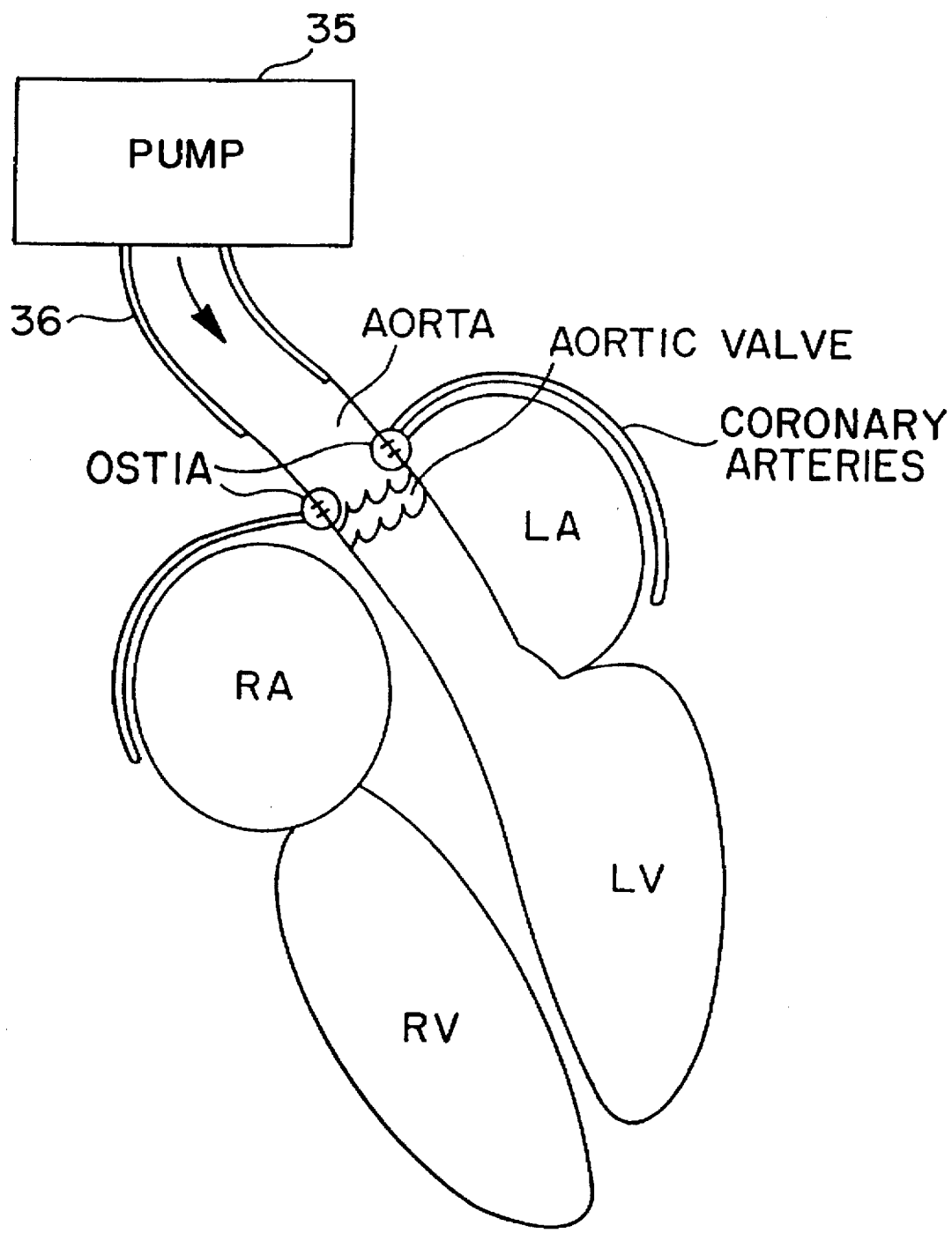
FIG. 1 is a schematic drawing of a human heart and the manner of introducing perfusion fluid into the aorta for retrograde perfusion of the coronary arteries.

Reference is made to FIG. 1 for a background discussion of the human heart, and the manner of providing retrograde perfusion of the heart. The heart is illustrated schematically, FIG. 1 showing the left atrium (LA), the left ventricle (LV), the right atrium (RA) and the right ventricle (RV). The aorta is illustrated ascending from the left ventricle, with the aortic valve being between the left ventricle and the aorta. In the aortic root, just distal from the valve, are the ostia, openings which pass blood to the coronaries (which are illustrated schematically). In retrograde perfusion, the perfusion fluid is provided from a pump 35, and supplied through a connection element or tube 36 to the aorta, so that the fluid is pumped through the ostia. Note that it doesn't matter if fluid doesn't pass through the aortic valve, which would normally be closed due to the back pressure of the fluid; the object is to perfuse the coronary arteries, so that the myocardial muscle is refreshed, and catabolites are carried away. The contracting heart will, when completely submersed, suck perfusate into the left atrium (LA) through the openings of the pulmonary veins, and pump it through the left ventricle (LV) into the aorta, thus refreshing the LA and LV cavity fluid.

Figure 2:
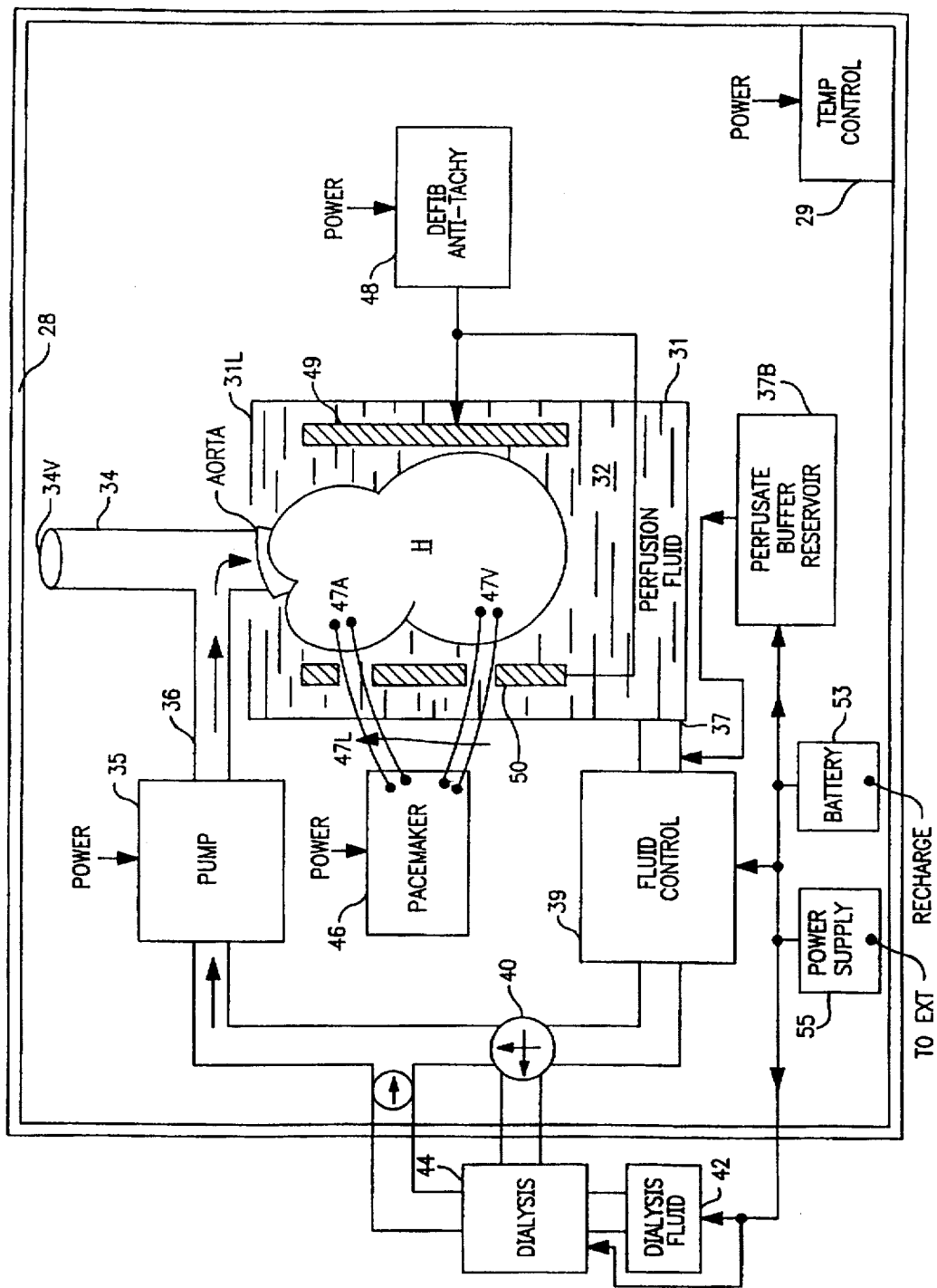
FIG. 2 is a schematic drawing of a preferred form of apparatus for preserving and maintaining a donor heart in accordance with this invention.

Referring now to FIG. 2, there is shown a schematic diagram of apparatus for preserving and maintaining a donor heart in accordance with this invention, and particularly for maximizing removal of catabolites. A housing 28 is provided, preferably of a size suitable for easy transportation and portable operation. The interior of the housing can be air, fluid up to a level below 31L, or other material such as isolation foam; the temperature is maintained by temperature control 29 (heater-cooler) at a temperature substantially the same as the temperature of the perfusion solution, e.g., in the range of 10-25 C. The heart itself is contained in or above a vessel 31, which holds perfusion liquid 32. For this system, where the heart is being paced and thus is beating, it is strongly preferable to maintain the heart fully submerged within the fluid, so as to prevent air-embolism through air sucking via the LA and LV. The vessel 31 is configured so that the heart fits easily in it without touching the walls, and is preferably covered with a lid 31L to prevent overspill and to prevent particles such as dust or other contamination from falling into the liquid. To accommodate hearts of the expected range of sizes, the vessel volume is in the range of about 0.5 to 2.0 liter. A factor influencing vessel size is that it is desired to keep the volume to a minimum because the perfusion fluid (e.g., perfluorochemical emulsions, hemoglobin enriched solutions) is very expensive. The size of the vessel is less important if crystalloid solutions are used. However, as discussed below, if the system is portable and dialysis is difficult during transportation, because of the required large volume of dialysis solutions, it may be desirable to increase the amount of perfusion fluid in the system so as to enable refreshing of the myocardium for an extended duration with a solution where the concentration of catabolites does not increase to levels toxic for the surrounding myocardial cells. Thus, the optimal amount of fluid in the system is subject to variation. A cradle or supporting net or sling (not illustrated) is also desirable within the vessel to prevent vigorous movements during transportation. The sling is suitably of a construction to avoid a compressive action onto the heart which would negatively affect coronary or interstitial perfusion.

The preferred fluid 32 is a perfluorochemical emulsion. See, for example, "Fluorochemical Emulsion APE-LM Substantially Improves Cardiac Preservation", Segel et al., *Am. J. Physiol.* 263: H730-H739, 1992. However, the invention is not limited in terms of the particular fluid employed.

Still referring to FIG. 2, there is shown a closed loop retrograde perfusion subsystem for circulating and processing the perfusion fluid. A pump 35 delivers the fluid under a substantially constant pressure through tube 36 to the aorta, as discussed above. Constant pressure can be maintained either by an open vertical tube portion 34 when there is a stable, vertical set-up, or by a valve 34V where the situation is unstable, as during transportation. Overspilled fluid is re-directed into the vessel. The input flow of fluid to the aorta is matched by the outflow at outlet 37, which connects to fluid control subsystem 39, and optimally by adding fluid from a buffer-reservoir 37B which contains fresh perfusate. Subsystem 39 performs a plurality of functions, using standard components and hardware, it being understood that a microprocessor and suitable software can also be utilized for control purposes, all within the state of the art. Components of control subsystem 39 may be combined compactly or provided as separate parts which are implemented in the system, as a matter of design choice.

Control subsystem performs the functions of fluid temperature control (cooling or heating the perfusion fluid to the range of 10–25 C.) and oxygenation; it may also perform other functions such as pH control, dialysis, bubble-or preferentially membrane- or hollow fiber-oxygenating, and other filtering. As illustrated in FIG. 2, there is optionally a separate dialysis unit 44 combined with reservoir 42 which provides the necessary dialysis solution, which unit 44 may be connected to receive fluid from subsystem 39 when two-way valve 40 connects them directly. Thus, in normal operation when sufficient power is available through power supply 55 connected to an external power line, the dialysis step is performed on the fluid at block 44, after the fluid has been operated on at control block 39. Note that dialysis can be withheld for a certain duration where the apparatus is in transit, e.g., on an airplane, in which case the apparatus is being powered only by battery 53. Under such portable circumstances, the fluid from control 39 is transferred through valve 40 so as to bypass dialysis unit 44, which is not used. As shown, an extra (exchangeable) fluid tank 37B may optionally be inserted into the circuit, to provide a larger refreshed supply of perfusion fluid for the purpose of extending the safe transit time. As is understood, the use of the dialyzer can be temporarily suspended when the unit is operating in a lower power battery, or portable mode. During such suspended duration, the fluid is continually being circulated and refreshing the myocardium. Although the catabolites are being removed from the interstitial spaces, where their toxic effect can cause damage, there is some build-up of these catabolites in the fluid. As long as the volume of fluid is great enough to keep the catabolites well diluted, there is not a problem; but clearly the potential build-up of catabolites is a limitation on the length of time that the portable operation without dialysis can be maintained. By providing the option of inserting a canister, or additional exchangeable tank of fluid 37B in series or parallel to the perfusion system, there is provided the capability of extending the useful duration of portable operation.

Still referring to FIG. 2, reference is made to the pacemaker, shown at 46, which is a critically important feature of this invention. The pacemaker is preferably a dual chamber pacemaker, operable in DDD mode, of the type made by the assignee of this invention, Medtronic, Inc.; alternately, it can be a quadruple chamber pacemaker providing 4-chamber asynchronous pacing modalities. The pacemaker pulses are delivered over leads 47L to electrodes 47A in the right atrium and 47V in the right ventricle, in standard fashion; for a quadruple pacemaker, an additional pair of electrodes is used. Screw-in pacing electrodes are one preferred embodiment, but patch or other forms of electrodes can also be used. Although bipolar electrodes are illustrated, it is to be understood that unipolar or multipolar electrodes can be also be used. The pacemaker has a standard rate control feature, operator controllable, and for use in this invention dealing with a human heart the rate is set for pacing the heart at a low rate less than normal pacing rates, preferably within the range of 2–40 bpm, and more preferably within a range of 15–20 bpm. In accordance with the available pacemaker art, heart parameters can be monitored, and data stored, so as to provide a history of cardiac condition during the preservation. As stated above, these low rates are most effective in combination with moderate hypothermia, i.e., 10–25 C., for contracting the heart to promote removal of the catabolites from the myocardium without raising the rate too high to limit catabolism. Also illustrated in FIG. 2 is a defibrillator 48 of standard type, which monitors the heart and delivers a defibrillation pulse (or pulses) across defibrillation electrodes 49. Alternately, both the pacemaker and the defibrillator can be provided by a combined PCD type device, also as made by Medtronic, Inc. Anti-tachycardia pacing therapies can be delivered through the pacing electrodes to prevent atrial and/or ventricular arrhythmias. It is to be understood that the defibrillation/anti-tachy device 48 has a suitable control portion by which the operator can adjust the treatment pulse(s) delivered.

Figure 3:
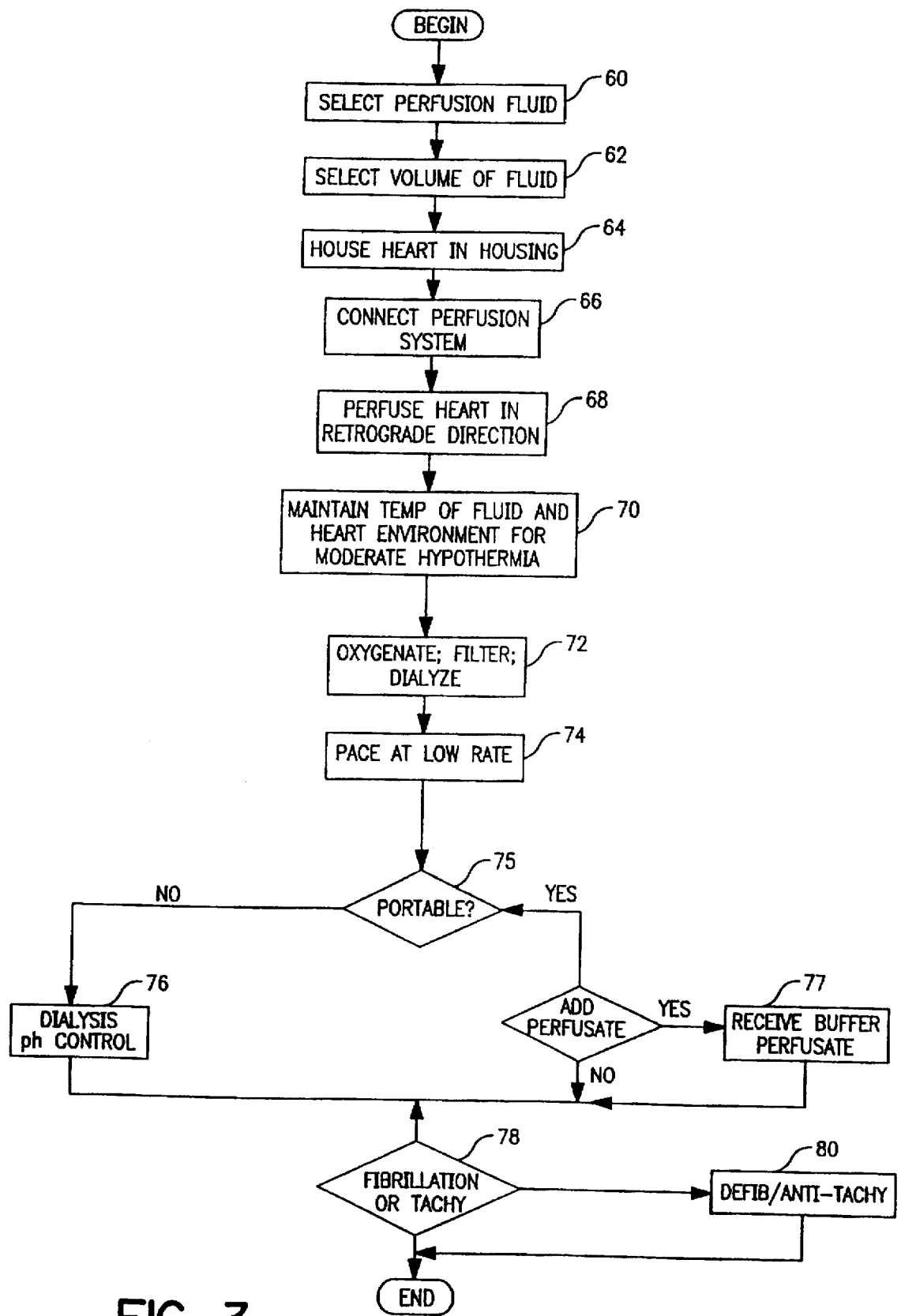
FIG. 3 is a flow diagram setting forth the primary functions carried out by the method and apparatus of this invention.

Referring now to FIG. 3, there is shown a flow diagram of the primary steps performed in carrying out the invention. As illustrated at block 60, the desired perfusion fluid is selected, e.g., a fluorochemical emulsion. Next, at 62, the volume of fluid, and the size of the heart-containing vessel are selected, according to the above-stated considerations. At 64, the heart is suspended, preferably submerged in the vessel, and then at 66 is connected to the closed loop perfusion system. As shown at 68, the heart is perfused in a retrograde manner, introducing the fluid so that it flows through the ostia into the coronary arteries. As seen at 70, the heart is maintained in a moderate hypothermic state by cooling the perfusion fluid to a temperature preferably in the range of 10–25 C., and also by controlling the environment around the vessel where the heart is submerged. The circulated fluid is oxygenated and filtered at 72; if there is no option concerning dialysis, the dialysis step is also performed. The heart is paced, at 74, at a low rate in the range of about 2–40 bpm. At 75, it is determined whether the apparatus is operating in the portable mode; if no, dialysis and pH control are performed at 76. Of course, it is understood that when the portable apparatus has sufficient power, then dialysis can be maintained during transportation as well, and dialysis and pH control are performed as illustrated at 72. Following a determination of portable operation at 75, a decision is made at 77 as to increasing the supply of perfusion fluid being used if dialysis is not being performed. If the fluid volume is to be increased, this is done at block 79. At block 78, the heart is continuously monitored to determine if there is fibrillation or another arrhythmia; if yes, a defibrillation shock or other suitable anti-tachycardia therapy is delivered as shown at 80.

There has been illustrated a system and method of preserving a donor heart which provides improved means for removing catabolites, thus both extending the available time for transportation, and improving the chances of delivering a fully functional heart upon transplant. Normally, during transport a 12 volt or other battery supply is provided, which should be used only when a power connection is not available, i.e., battery use should be limited to periods of hand-held transportation, with the battery recharged when power is again available. The processes of oxygenation, dialysis and filtering are used when it is desired to prolong preservation time, and need not be used when considered unnecessary.

What is claimed is:

1. Apparatus for preservation of a heart for subsequent transplantation, said heart including a portion of the aorta outside of the aortic valve, comprising:

a heart-containing vessel and perfusion fluid in said vessel, said vessel adapted to contain a heart, said heart being submerged in said perfusion fluid;

a perfusion fluid circulating system for circulating said perfusion fluid in a retrograde direction through coronary arteries of the submerged heart, said system having input means for inputting said fluid to the aorta above the aortic valve so that at least some of said fluid is perfused into the coronary ostia and through the coronary arteries;

output means for outputting said fluid from said vessel;

pump means for pumping said fluid with a substantially constant pressure into said input means;

processing means for processing said fluid to control predetermined parameters of said fluid; and pacing system means for pacing said heart, said pacing system means having pulse generator means for generating pace pulses at a rate below the normal pacing range for a human heart, and lead means for delivering said pace pulses to said heart.

2. The apparatus as described in claim 1, wherein said pulse generator means has rate means for generating pace pulses at a rate in the range of 2–40 bpm.

3. The apparatus as described in claim 1, wherein said processing means comprises temperature means for controlling the temperature of said fluid so as to maintain said heart in a state of moderate hypothermia.

4. The apparatus as described in claim 1, wherein said processing means comprises dialysis means for cleaning ions or molecules such as catabolites from said fluid.

5. The apparatus as described in claim 1, wherein said pacing system comprises pace control means for controlling said pulse generator means to generate pace pulses asynchronously.

6. The apparatus as described in claim 1, wherein said pacing system means comprises a pacemaker operating in one of the DDD or quadruple chamber modes.

7. The apparatus as described in claim 1, further comprising anti-arrhythmia means for delivering an anti-arrhythmia treatment when said heart has an arrhythmia.

8. The apparatus as described in claim 1, wherein said vessel has a volume of 0.5 to 2.0 liters.

9. The apparatus as described in claim 1, wherein said processing means comprises temperature means for controlling the temperature of said fluid at a temperature within a range of 10–25 degrees centigrade.

10. The apparatus as described in claim 1, comprising sling means to provide support to said heart.

11. The apparatus as described in claim 1, comprising a battery supply, and wherein said apparatus is portable.

12. The apparatus as described in claim 1, wherein said lead means comprises at least one screw-in pacing electrode for delivering said pace pulses to said heart.

13. The apparatus as described in claim 1, wherein said fluid is selected as one of a perfluorochemical or an hemoglobin enriched solution.

14. The apparatus as described in claim 1, wherein said processing means comprises dialyzer means for carrying out the function of dialysis on said fluid, and select means for selecting when said dialyzer means is operable.

15. A system for preservation of a donor human heart and which efficiently removes catabolites from said heart, comprising:

pacing means for pacing said heart at a rate in the range of 2–40 bpm, said pacing causing cardiac contractions which promote removal of catabolites from myocardial areas of said heart, perfusion means for perfusing perfusion fluid through coronary arteries of said heart, and cleaning means for cleaning said catabolites from said fluid.

16. The system as described in claim 15, comprising temperature control means for maintaining said heart in a moderate hypothermic state.

17. The system as described in claim 16, wherein said perfusion means comprises a perfusion fluid of the extracellular type without cardioplegic properties.

18. The system as described in claim 17, wherein said temperature means comprises means for controlling the temperature of said fluid at a temperature within the range of about 10–25 degrees centigrade.

19. The system as described in claim 18, further comprising portable power means for providing battery power to said system so that it is portable.

20. The system as described in claim 19, further comprising back-up perfusion fluid supply means for providing a back-up supply of additional perfusion fluid for use when said system is portable.

21. A method of preserving a donor heart with minimum accumulation of catabolites in the cardiac myocardium, comprising:

housing said heart in a perfusate solution, maintaining said heart in a moderate hypothermic state, and pacing said heart at a relatively low rate.

22. The method as described in claim 21, further comprising perfusing said heart with said perfusion fluid in a retrograde manner.

23. The method as described in claim 22, comprising cooling said fluid so as to maintain said heart at a temperature in the range of 10–25 C., and pacing said heart at a rate within the range of 2–40 bpm.

24. The method as described in claim 22, comprising pacing said heart at a rate within the range of 2–40 bpm.

25. The method as described in claim 21, comprising dialyzing said fluid.

26. The method as described in claim 21, comprising said perfusion fluid as a perfluorochemical emulsion.

27. The method as described in claim 21, comprising submerging said heart in said perfusion fluid.

28. Apparatus for preserving and maintaining a donor heart with minimal build-up of catabolites, comprising:

housing means for housing said heart;

hypothermia means for maintaining said heart in a hypothermic state, the hypothermia means coupled to the housing means;

perfusion means for perfusing said heart with a perfusion fluid, the perusion means coupled to the housing means; and pacing means for pacing said heart to contract at a below normal pacing rate, the pacing means coupled to the housing, whereby said contraction promotes removal of toxic products of metabolism from the interstitial spaces of the heart myocardium.

29. The apparatus as described in claim 28, wherein said pacing means has rate control means for controlling the pacing rate to a rate within the range of 2–40 bpm.

30. The apparatus as described in claim 28, wherein said apparatus has a battery supply for portable operation, and comprising means for increasing the supply of said perfusion fluid.

* * * * *